United States Patent [19]

Cornelius et al.

[11] Patent Number: 5,650,155
[45] Date of Patent: Jul. 22, 1997

[54] TOCOLS AS ADJUVANT IN VACCINE

[75] Inventors: Lammert Cornelius; Eric Onno Rijke, both of Boxmeer, Netherlands

[73] Assignee: AKZO Nobel N.V., Arnhem, Netherlands

[21] Appl. No.: 320,202

[22] Filed: Oct. 7, 1994

Related U.S. Application Data

[63] Continuation of Ser. No. 7,400, Jan. 21, 1993, abandoned, which is a continuation of Ser. No. 474,434, Feb. 2, 1990, abandoned.

[30] Foreign Application Priority Data

Feb. 4, 1989 [NL] Netherlands .................. 8900277

[51] Int. Cl.$^6$ .................. A61K 9/107; A61K 39/12; A61K 31/355
[52] U.S. Cl. .................. 424/283.1; 424/204.1
[58] Field of Search .................. 424/204.1, 283.1

[56] References Cited

U.S. PATENT DOCUMENTS

| | | | |
|---|---|---|---|
| 3,919,411 | 11/1975 | Glass et al. | 424/283.1 |
| 4,650,677 | 3/1987 | Roerink et al. | 424/89 |
| 4,772,466 | 9/1988 | Allison et al. | 424/88 |
| 4,788,056 | 11/1988 | Lutticken et al. | 424/283.1 |
| 5,151,267 | 9/1992 | Babiuk et al. | 424/283.1 |

FOREIGN PATENT DOCUMENTS 8702219  4/1987  WIPO .................. A01N 25/28

OTHER PUBLICATIONS

Merck Index, pp. 1290, 889, 327, (1976).
Tengerdy, et al, 1983, "Vitamin–E Enhanced Humoral Antibody . . . " Br. Vet. J. 139:147–152.
Allison, et al, 1988, "An Adjuvant Formulation for Use with . . . " Technological Advances in Vaccine Development, pp. 401–409.
Afzal, et al, 1984, "Protection of Rams Against Epididymitis . . . " Vet. Immunol. & Immunopath 7:293–304.
Tengerdy, et al, 1983, "Vitamin–E Enhanced Humoral . . . " British Veterinary Journal 139:147–52.
Franchini, et al., 1988 "Use of Vitamin E in the Preparation . . . " Clinica Veterinaria 111:121–133.

*Primary Examiner*—Michael P. Woodward
*Attorney, Agent, or Firm*—Mary E. Gormley

[57] ABSTRACT

Oil based vaccines often cause serious local side effects at the site of administration and/or have a high viscosity which make said vaccines difficult to handle. Vaccines comprising as an adjuvant a stable emulsion of tocols in water do not display these undesired effects and induce good immune responses.

8 Claims, 2 Drawing Sheets

TOCOLS AS ADJUVANT IN VACCINE

This is a continuation of U.S. Ser. No. 08/007,400, filed Jan. 21, 1993, now abandoned, which is a file wrapper continuation of U.S. Ser. No. 07/474,434, filed Feb. 2, 1990, now abandoned.

The invention relates to a vaccine which contains a stable emulsion with tocols and to the method for the preparation of such a vaccine.

BACKGROUND OF THE INVENTION

For protection against transmittable infectious diseases it is customary to vaccinate humans and animals with immunogenic material against which protective anti-bodies can be formed.

For this purpose, for example, the pathogen itself can be administered in a live, but preferably non-infectious form, or the killed pathogen or an antigen fraction of the pathogen in which the infectious component is lacking can be administered.

In these latter two cases it is necessary also to add to the antigen one or more components which stimulate the immune response of the organism to be protected. Such immune response-stimulating components are usually referred to by the term adjuvants. Freund's complete adjuvant is a water-in-oil (w/o) emulsion of mineral oil and killed mycobacteria and is regarded as one of the most powerful adjuvants. Other known adjuvants are emulsions of mineral oils, such as Freund's incomplete adjuvant, and of vegetable oils, such as peanut oil, maize oil, cottonseed oil and sunflower oil, and semi-synthetic oils, such as MIGLYOL™ 812N and MYRITOL™ oil.

However, the abovementioned emulsions, especially water-in-oil emulsions based on mineral oil, cause serious tissue irritations, inflammation swellings and cysts at the site of administration, for which reason the routine use of these emulsions in humans and animals is less desirable and in certain cases is even prohibited. Moreover, vaccines based on w/o emulsions are relatively viscous, which makes injection of the vaccine more difficult.

Reducing the oil content causes such a rise in the viscosity that the vaccine can no longer be injected. At the same time this can have an effect on the stability of the emulsion.

The use of α-tocopheryl acetate as a water-in-oil emulsion in a vaccine for the protection of rams against infection with Brucella ovis was described by Afzal et al., Veterinary Immunology and Immunopathology 7 (1984), 293–304. However, the vaccine contains approximately 50% dl-α-tocopheryl acetate, as a result of which the vaccine becomes viscous and consequently is difficult to handle.

SUMMARY OF THE INVENTION

The aim of the present invention is thus to provide a vaccine which does not cause undesired local effects in humans or animals of the type described above and at the same time is easy to handle.

The vaccine according to the invention is characterized in that it contains a stable emulsion of tocols as adjuvant in water.

Surprisingly it has been found that an oil-in-water emulsion of a tocol derivative of this type couples the favourable characteristic of a low viscosity, and thus easier handling, with an adjuvant action which is at least as good as that of a water-in-oil emulsion which contains a corresponding tocol derivative. This result is surprising in view of the fact that it is known that oil-in-water emulsions are less good adjuvants than water-in-oil emulsions (Herbert, W. J., The mode of action of mineral-oil emulsion adjuvants on antibody production in mice, Immunology 14 (1968), 301–318 and Herbert, W. J., Mineral-oil adjuvants and the immunization of laboratory animals, in: Handbook of experimental immunology Vol. 3, ed. by D. M. Weir, third edition, Blackwell 1979).

The vaccine according to the invention consequently contains a stable oil-in-water emulsion with good adjuvant characteristics, causes no adverse local effects after administration and is readily injectable.

DESCRIPTION OF THE PREFERRED EMBODIMENTS

Figure 1:
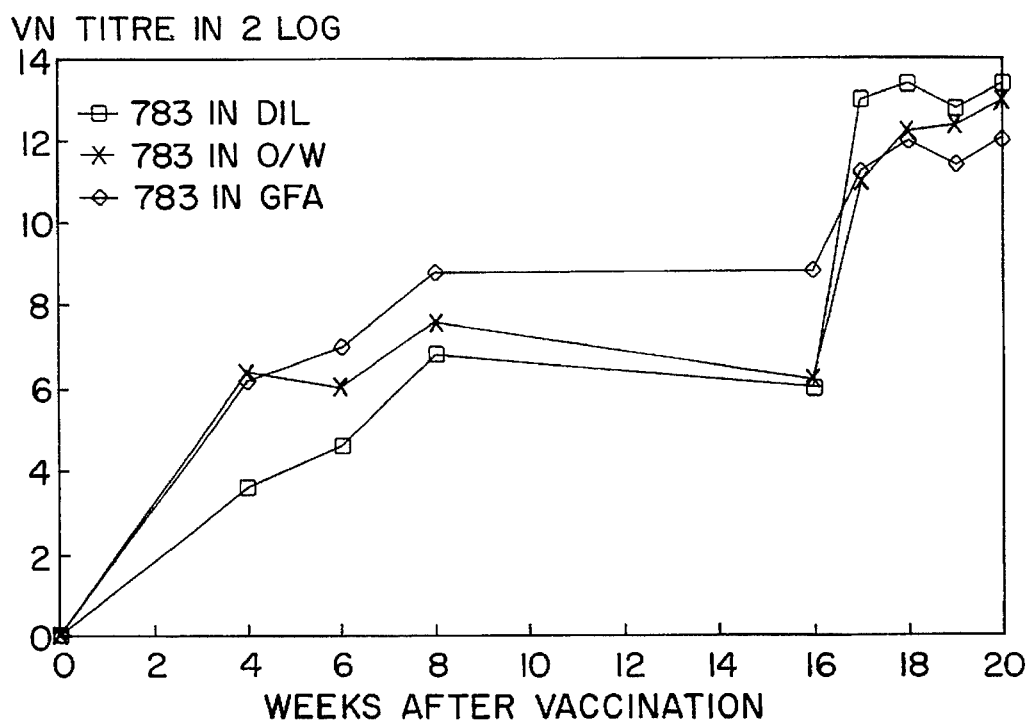

Tocols which can be used as adjuvant according to this invention are understood to mean tocol and derivatives of tocol. Tocol and derivatives hereof can be represented by the general formula I:

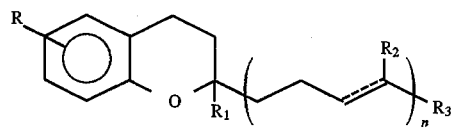

wherein
R may be H or one or more of identical or different substituents chosen from the group comprising alkyl, alkoxy, acyloxy, hydroxy, a sulphate and a phosphate group;
$R_1$ and $R_3$ independently of one another are H or alkyl;
$R_2$ is H or alkyl and may be different in each unit;
the broken line indicates the presence or absence of an additional carbon-carbon bond in a unit; and
n=has the value 1 to 10.

The alkyl group in R, $R_1$, $R_2$ and $R_3$ may be chosen in particular from a linear or branched carbon chain having 1–4 carbon atoms, such as methyl, ethyl, butyl or isobutyl.

The compound tocol is represented by the formula

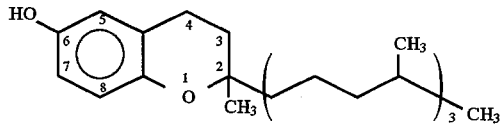

Tocol derivatives are, inter alia: 5-methyltocol, 7-methyltocol, 8-methyltocol, 5,7-dimethyltocol, 5,8-dimethyltocol, 7,8-dimethyltocol, 5,7,8-trimethyltocol, 8-methyltocotrienol, 7,8-dimethyltocotrienol, 5,8-dimethyltocotrienol, 5,7,8-trimethyltocotrienol, 5,7-diethyltocol, 5,7-dimethyl-8-ethyltocol, 5,7-diethyl-8-methyltocol, the esters, such as formates, acetates, succinates and nicotinates, the sulphates and phosphates, and also the ethers, such as the methyl and ethyl ethers of these compounds, and 6-desoxytocol.

A preferred class of tocols to be used in the present invention may be represented by the general formula III:

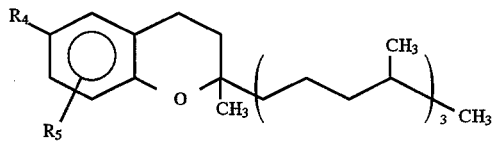

wherein:
$R_4$ may be hydroxy, an acyloxy group, said group preferably being derived from an aliphatic or aromatic carboxylic acid with 1–8 carbon atoms, or a sulphate or phosphate group, $R_5$ may be H or one up to three identical or different alkyl groups with 1–4 carbon atoms.

More in particular, tocol and esters thereof as well as 5,7,8-trimethyltocol (Vitamin-E) and esters thereof according to the general formula III can advantageously be applied in a vaccine according to the present invention.

A very suitable tocol derivative according to this invention is 5,7,8-trimethyltocol acetate ($\alpha$-tocopherol acetate). In practice the racemate, dl-$\alpha$-tocopherol acetate, is usually employed, although it is also possible to use the optically active compound.

The concentration of tocols in vaccines according to the invention is preferably about 0.1–40% by weight and in particular about 2.5–10.0% by weight.

It is also possible to use a mixture of two or more different tocols with adjuvant action in a vaccine. In addition to tocol or a derivative hereof, the emulsion may contain further components having an adjuvant action.

Suitable further components are, for example, avridin, carbomers, non-ionic block polymers and muramyl dipeptides.

An emulsifier which can be used in the stable emulsion according to this invention can be chosen from the group of emulsifiers which are customarily used for the present purpose. Suitable emulsifiers are, inter alia, non-ionic surfactants, such as polyoxyethylene sorbitan mono-oleate, polyoxyethylene monolaurate, polyoxyethylene fatty acid esters, such as polyoxyethylene stearate, polyoxyalkyl ethers, such as polyoxyethylene cetyl ether, polyoxyethylene castor oil derivatives, polyvinyl-pyrrolidone, polyvinyl alcohol, carboxymethylcellulose, lethicin and gelatin; anionic surfactants including salts of alkyl sulphate esters, such as sodium lauryl sulphate; cationic surfactants and amphoteric surfactants. The concentration of the emulsifier according to the invention is preferably between 0.1 and 20% and more particularly between 2.5 and 7.5% by weight.

The vaccine may be prepared by means of emulsifying tocols with immunogenic material containing an aqueous solvent. In another embodiment the vaccine is prepared by means of emulsifying tocols with an aqueous solvent, after which the emulsion is mixed with immunogenic material. It is also possible, for the preparation of a vaccine according to the invention, to use as the starting material tocols to which immunogenic material has been added, which are then emulsified with an aqueous solvent.

The vaccine is preferably prepared by mixing tocols with an emulsifier, after which this mixture is emulsified with water. Immunogenic material is added to the emulsion thus obtained, by which means the desired stable emulsion is finally formed. It is desirable for the physical stability of the vaccine that the dispersed particles of tocols have a certain size. It has been found that the physical stability manifests itself best if the dispersed particles are preferably smaller than 20 µm and more particularly smaller than 1 µm.

The vaccine according to the invention is suitable for use of live and non-live material as immunogen. Non-live antigen material may be selected from killed pathogens or immunogenic fractions (subunits) thereof. The vaccine is also suitable for generating an immune response against non-pathogenic substances, for example for the production of antisera for use in diagnostic tests and for immunological sterilization or castration.

The pathogens can be, for example: viruses, bacteria or parasites. These can be killed by chemical or by physical means. In this context killing signifies inactivation, for example by such a change in the genetic material and/or other vital components that the pathogen is no longer capable of reproduction. Suitable chemical agents for killing pathogens are, for example, formaldehyde, glutaraldehyde, β-propiolactone, ethyleneimine and derivatives, or another compound which can react bifunctionally or multifunctionally with reactive groups belonging to the pathogen. Physical agents for killing pathogens are, for example, UV radiation, γ radiation, "heat shock" and X-radiation.

Antigen fractions of the abovementioned pathogens or of non-pathogenic substances can be obtained therefrom by means of chemical or physical methods, and, if desired, followed by separation of a fraction with the aid of chromatography, centrifuging and similar techniques. After these operations components are obtained which, although very pure if desired, frequently will also have poor immunogenicity. If desired, these components of pathogens or non-pathogenic substances can be bound to a carrier (for example "keyhole limpet" hemocyanin or liposomes or other micellar complexes) in order to increase the immunogenicity. The abovementioned term "immunogenic fractions of pathogens or non-pathogenic substances" is also used to signify: synthetic antigens or haptens, with which natural antigens of the pathogen or non-pathogenic substances in question are imitated. Synthetic antigens or haptens of this type can be prepared in a known manner with the aid of organic synthetic methods or in the case of, for example, polypeptides with the aid of recombinant DNA methods.

The concentration of antigen in a vaccine according to the invention is in general 1–85% by weight.

In addition to a vaccine of this type which contains immunogenic material from only one pathogen (so-called monovalent vaccines), vaccines which contain immunogenic material from several pathogens (so-called combination vaccines) likewise fall within the scope of the invention. Combination vaccines of this type contain, for example, material from various viruses or from various strains of a single virus or from virus/bacterium combinations or various bacteria. Combination vaccines of this type can also contain material from parasites.

EXAMPLE 1

To prepare a vaccine against Gumboro's disease, 7.5 g of vitamin E acetate and 5.0 g of POLYSORBATE™ 80 are mixed together with continuous stirring. This mixture is then made up to 50 g with distilled water. The vaccine is prepared by mixing 50 g of the above mixture with 50 g of an aqueous solution of inactivated immunogenic material, with stirring, so that the vaccine finally contains 18.2% (weight per unit volume) Gumboro virus antigen.

EXAMPLE 2

Three groups of 10 four-week-old SPF chickens were vaccinated intramuscularly with 0.5 ml of vaccine containing inactivated Gumboro virus ($10^{7.3}$ $TCID_{50}$/ml) prepared according to Example 1. Blood was taken 4, 8, 12, 16 and 20 weeks after vaccination, after which antibody titres were determined in the serum by means of an ELISA (incubation with virus-coated microtitre plate+chicken serum; incubation with anti-chicken-Ig's antibodies-enzyme conjugate).

| | Antibody response after (weeks post-vaccination) | | | | |
|---|---|---|---|---|---|
| Vaccine | 4 | 8 | 12 | 16 | 20 |
| saline solution | 7.2 ± 2.2[a] | 7.1 ± 2.2 | 6.8 ± 1.6 | 7.3 ± 1.7 | 7.6 ± 1.4 |
| vit. E acetate[b] | 12.6 ± 2.1 | 11.5 ± 1.3 | 9.3 ± 1.5 | 9.4 ± 1.3 | 9.0 ± 1.3 |
| mineral oil[c] | 10.0 ± 1.3 | 11.9 ± 1.4 | 11.5 ± 0.9 | 11.4 ± 0.7 | 10.9 ± 1.1 |

[a] mean ELISA titre ($^2$log) with standard deviation
[b] 7.5% by weight o/w emulsion
[c] Freund's incomplete w/o emulsion.

EXAMPLE 3

Two groups of 10 five-week-old mice were vaccinated intramuscularly with 0.1 ml of vaccine containing inactivated Aujeszky virus, prepared analogously to Example 1 ($10^8$ TCID$_{50}$/ml) Blood was taken 4, 8 and 12 weeks after vaccination, after which antibody titres were determined in the serum by means of an ELISA (incubation with virus-coated microtitre plate+mouse serum; incubation with anti-mouse-Ig's antibodies-enzyme conjugate).

| | Antibody response after (weeks post-vaccination) | | |
|---|---|---|---|
| Vaccine | 4 | 8 | 12 |
| saline solution | 11.7 ± 1.2[a] | 11.2 ± 1.3 | 11.3 ± 1.6 |
| vit. E acetate[b] | 13.2 ± 1.2 | 13.1 ± 1.8 | 13.1 ± 1.5 |

[a] mean ELISA titre ($^2$log) with standard deviation
[b] 7.5% by weight o/w emulsion.

EXAMPLE 4

Groups of 10 four-week-old SPF chickens were vaccinated intramuscularly with 0.5 ml of vaccine containing purified *E. coli*-F11-pilus protein (20 μg/dose), prepared analogously to Example 1. Blood was taken 4, 8, 12 and 16 weeks after vaccination, after which antibody titres were determined in the serum by means of an ELISA (incubation with *E. coli*-F11-pilus-protein-coated micro-titre plate+ chicken serum; incubation with anti-chicken-Ig's antibodies-enzyme conjugate).

| | Antibody response after (weeks post-vaccination) | | | |
|---|---|---|---|---|
| Vaccine | 4 | 8 | 12 | 16 |
| saline solution | 5.9 ± 1.4[a] | 8.3 ± 2.4 | 8.6 ± 2.2 | 7.2 ± 0.8 |
| vit. E-acetate[b] | 10.5 ± 0.8 | 14.5 ± 0.0 | 13.3 ± 0.9 | 12.0 ± 1.6 |
| mineral oil[c] | 9.9 ± 2.8 | 13.5 ± 2.3 | 13.5 ± 1.8 | 12.3 ± 1.3 |

[a] mean ELISA titre ($^2$log) with standard deviation
[b] 7.5% by weight o/w emulsion
[c] Freund's incomplete w/o emulsion.

EXAMPLE 5

In the same experiment as described in Example 4 chickens were also vaccinated with a water-in-oil emulsion with vitamin E acetate, based on castor oil. The result of this is compared with the oil-in-water emulsion with vitamin E acetate from Example 4.

| | Antibody response after (weeks post-vaccination) | | | | |
|---|---|---|---|---|---|
| Vaccine | 4 | 8 | 12 | 16 | 20 |
| w/o-emulsion[b] | 9.8 ± 1.1[a] | 11.8 ± 1.5 | 12.0 ± 1.6 | 10.6 ± 1.2 | 9.0 ± 1.1 |
| o/w-emulsion[c] | 10.5 ± 0.8 | 14.5 ± 0.8 | 13.3 ± 0.9 | 12.0 ± 1.6 | 10.0 ± 1.1 |

[a] mean ELISA titre ($^2$log) with standard deviation
[b] 7.5% vitamin E acetate + castor oil (50%)
[c] 7.5% vitamin E acetate.

EXAMPLE 6

This example is to demonstrate the adjuvant activity of tocol and derivates thereof in a stable oil-in-water emulsion. The adjuvant potency of said compounds is illustrated in the table shown below using the purified *E. coli*-FII-pilus protein as an antigen. The experiments were carried out exactly as described in Example 4.

| | Antibody response after (weeks post-vaccination) | | |
|---|---|---|---|
| Vaccine | 4 | 8 | 12 |
| saline solution | 7,7 ± 1,6[a] | 9,0 ± 1,9 | 9,0 ± 1,6 |
| vit. E acetate[b] | 12,1 ± 0,7 | 12,4 ± 0,7 | 11,8 ± 0,9 |
| vit. E nicotinate[b] | 10,2 ± 1,5 | 11,9 ± 1,1 | 11,6 ± 1,0 |
| tocol[b] | 12,0 ± 1,7 | 11,9 ± 0,6 | 11,4 ± 0,8 |
| controls | 5,4 ± 0,6 | 5,9 ± 1,1 | 6,6 ± 1,0 |

[a] mean ELISA titre ($^2$log) with standard deviation
[b] 7,5% by weight o/w emulsion.

EXAMPLE 7

Groups of 5 pigs seronegative for pseudorabies and 4–6 weeks of age were housed in an isolation unit. Pigs were vaccinated once with a live pseudorabies vaccine (PRV strain 783) having a titre of the live component of $10^6$ TCID$_{50}$/dose. In all vaccinations one dose of 2 ml was given intramuscularly behind the ear.

As solvent for the live freeze-dried vaccines:

aqueous diluent (DILUVAE™, commercially available from International B.V., The Netherlands:dil)

mineral oil o/w emulsion (commercially available from International B.V., The Netherlands:o/w)

Vitamin-E acetate o/w emulsion (7,5% by weight Vit. E acetate):GFA, were used.

Blood samples were taken at the intervals indicated in FIG. 1. Serum samples were prepared and tested for the presence of virus neutralizing antibodies by ELISA. The challenge with 7 log TCID$_{50}$ of virulent pseudorabies strain 75V19 was done intranasally at 16 weeks after vaccination. Virus excretion and weight gain were monitored.

Results

Virus neutralizing antibodies

FIG. 1 shows the presence of virus neutralizing (VN) antibodies as a result of a vaccination with the three vaccines mentioned above. At the time of challenge the VN titre induced by the Vitamin-E acetate o/w vaccine was higher than those induced by the mineral oil o/w vaccine or the vaccine containing the aqueous diluent.

Virus excretion

Figure 2:
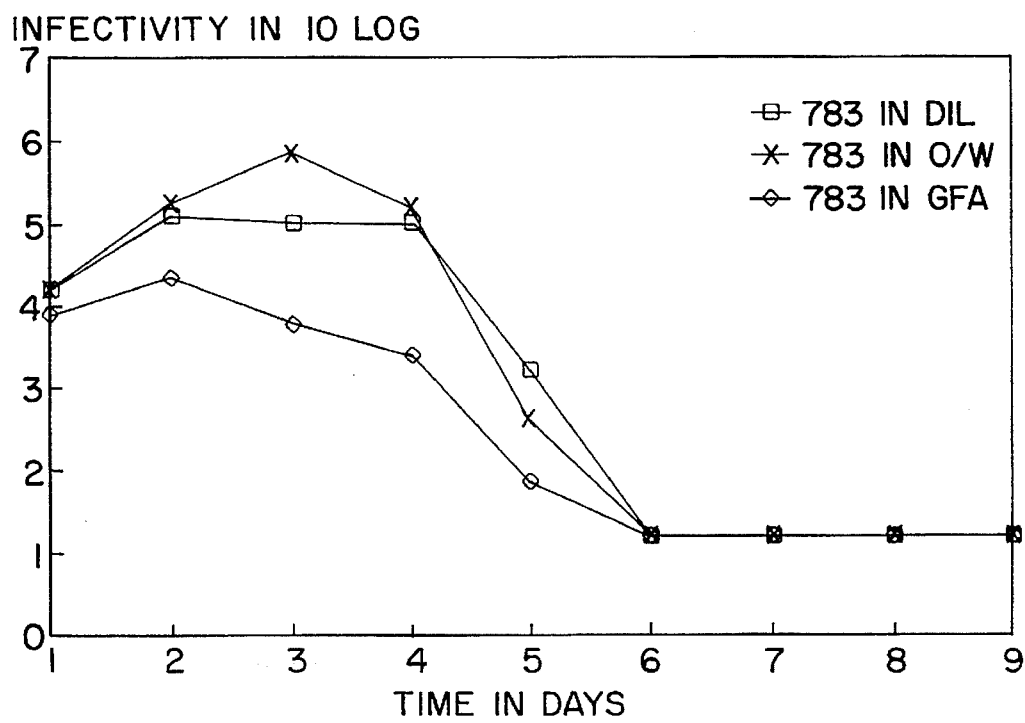

Nasal swabs were taken daily after challenge until at least on two consecutive days all the animals of a given group were shown to be negative in the test. The viral titres presented as $TCID_{50}$ per ml of nasal washing are shown in FIG. 2. Live PRV vaccine with a Vitamin-E acetate o/w adjuvant shows reduced virus titre, indicating another positive effect of this kind of adjuvant for live vaccines.

Weight gain

Figure 3:
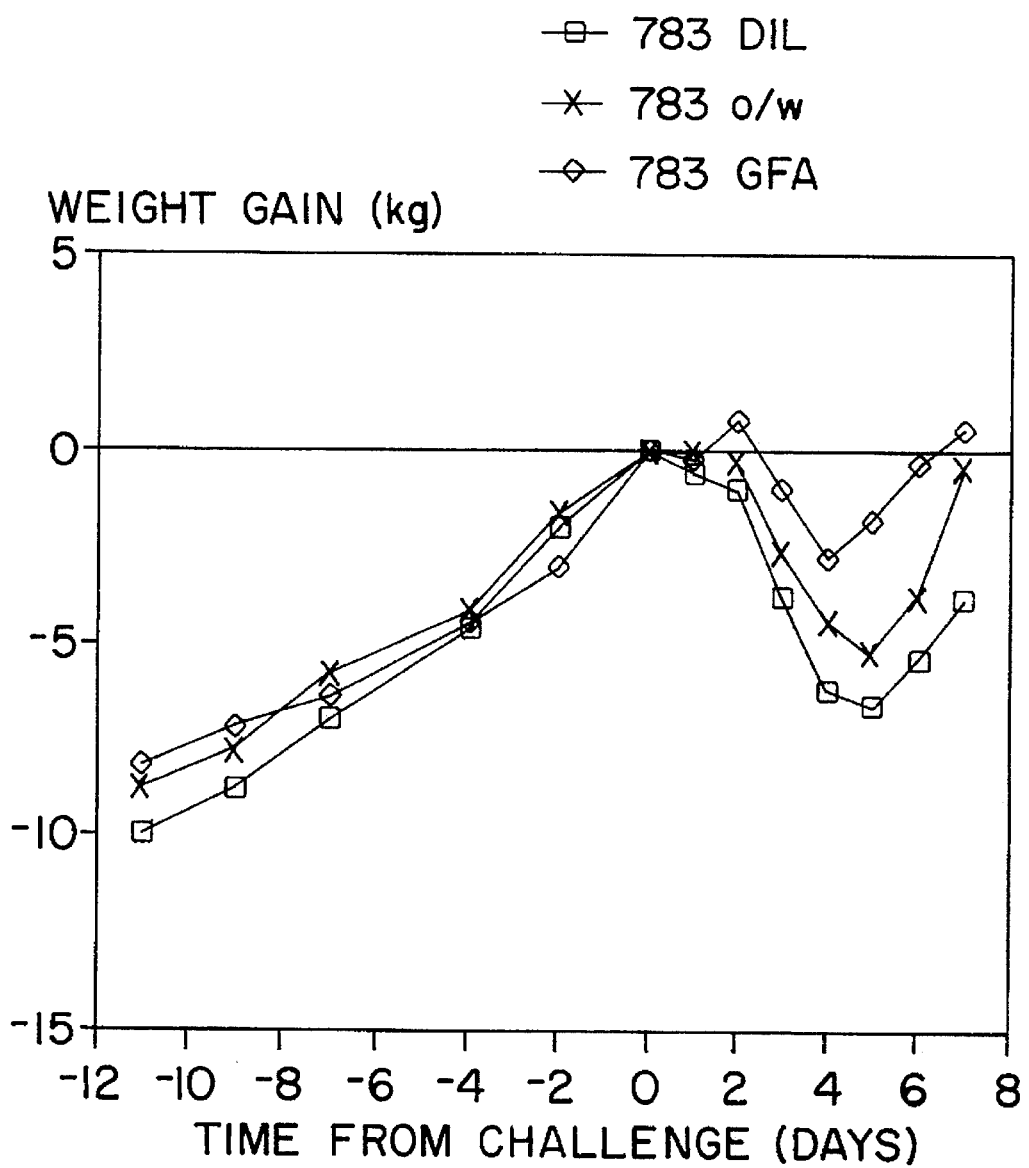

Body weights were determined at regular intervals before challenge, and from day of challenge body weights were measured daily (FIG. 3).
Calculations were performed to obtain the average daily weight gain (or loss) in percentage over the 7 days following challenge in accordance with the method prescribed by the European Pharmacopoeia (Draft European Pharmacopoeia, November 1988, Freeze-dried Aujeszky's disease live vaccine for pigs) as presented in the table below:

| Ranking | Vaccine | Remarks | Δ average percentage of growth per day (between day 0 and 7 p.c.) | |
|---|---|---|---|---|
| 1 | 783 | GFA | 1.55 | |
| 2 | 783 | o/w | 1.39 | |
| 3 | 783 | Diluvac | 0.78 | |
| 4 | Controls | — | 0.00 | (−1.45) |

The differences of each group to the control group is given. The animals of the control groups suffered a weight loss of 1.45% per day during 7 days (shown between brackets). From FIG. 3 and the table it should be concluded that the Vitamine-E o/w adjuvant is more effective in the live vaccine than the mineral oil o/w vaccine which in turn is more effective than the aqueous diluent.

We claim:

1. A vaccine comprising immunogenic material in an essentially mineral oil-free stable oil-in-water emulsion comprising tocols, wherein the vaccine contains from 0.1 to 40% by weight tocols and the tocols have the formula:

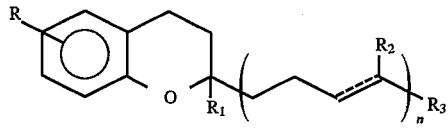

wherein:

R may be H or one or more of identical or different substituents chosen from the group consisting of alkyl, alkoxy, acyloxy, hydroxy, a sulphate and a phosphate group;

$R_1$ and $R_3$ independently of one another are H or alkyl;

$R_2$ is H or alkyl and may be different in each unit;

the broken line indicates the presence or absence of an additional carbon—carbon bond in a unit; and n has the value 1 to 10.

2. The vaccine according to claim 1, wherein the tocols have the formula:

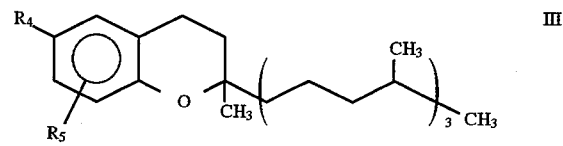

wherein:

$R_4$ may be hydroxy, an acyloxy group, a sulphate or a phosphate group; and $R_5$ may be H or one to three identical or different alkyl groups with 1–4 carbon atoms.

3. The vaccine according to claim 2, wherein the tocol is 5, 7, 8-trimethyltocol acetate.

4. The vaccine according to claim 1, further comprising at least one other component having adjuvant action.

5. The vaccine according to claim 1, wherein the vaccine contains from 2.5 to 10% by weight tocols.

6. The vaccine according to claim 1, wherein the tocols are in the form of dispersed particles and said particles are no larger than 20 µm.

7. An adjuvant mixture comprising a stable emulsion of tocols in water, wherein the tocols constitute 0.1 to 40% by weight of the adjuvant mixture.

8. The vaccine according to claim 5, wherein said particles are no larger than 1 µm.

* * * * *